(12) United States Patent
Bayer et al.

(10) Patent No.: US 11,266,491 B2
(45) Date of Patent: Mar. 8, 2022

(54) IMPLANT AND METHOD FOR PRODUCTION THEREOF

(71) Applicant: BIOTRONIK AG, Buelach (CH)

(72) Inventors: Ullrich Bayer, Admannshagen-Bargeshagen (DE); Bernd Block, Rostock (DE); Baerbel Becher, Rostock (DE); Daniel Lootz, Rostock (DE)

(73) Assignee: Biotronik AG, Buelach (CH)

( * ) Notice: Subject to any disclaimer, the term of this patent is extended or adjusted under 35 U.S.C. 154(b) by 218 days.

(21) Appl. No.: 15/880,274

(22) Filed: Jan. 25, 2018

(65) Prior Publication Data
US 2018/0161144 A1  Jun. 14, 2018

Related U.S. Application Data

(62) Division of application No. 13/764,267, filed on Feb. 11, 2013, now Pat. No. 9,913,707.
(Continued)

(51) Int. Cl.
| | |
|---|---|
| *A61F 2/07* | (2013.01) |
| *A61F 2/04* | (2013.01) |
| *A61F 2/82* | (2013.01) |
| *B21D 21/00* | (2006.01) |
| *C22C 23/00* | (2006.01) |
| *C22C 28/00* | (2006.01) |
| *C23C 10/22* | (2006.01) |

(Continued)

(52) U.S. Cl.
CPC .............. *A61F 2/04* (2013.01); *A61L 31/022* (2013.01); *B21C 23/002* (2013.01); *B21C 23/32* (2013.01); *B21D 21/00* (2013.01); *C10M 103/04* (2013.01); *C22C 23/00* (2013.01); *C22C 23/06* (2013.01); *C22C 28/00* (2013.01); *C23C 10/22* (2013.01); *A61F 2/02* (2013.01); *A61F 2/82* (2013.01); *C10M 2201/053* (2013.01); *C10N 2010/06* (2013.01); *C10N 2010/08* (2013.01); *C10N 2030/06* (2013.01); *C10N 2040/242* (2020.05)

(58) Field of Classification Search
CPC .. A61F 2310/00041; A61F 2310/00011; A61F 2/04; A61F 2/07; A61F 2/82; A61F 2310/000111; A61F 2/02; A61L 31/022; A61L 27/047
See application file for complete search history.

(56) References Cited

U.S. PATENT DOCUMENTS

| | | |
|---|---|---|
| 2,486,130 A | 10/1949 | Dietrich et al. |
| 3,125,222 A | 3/1964 | Foerster et al. |

(Continued)

FOREIGN PATENT DOCUMENTS

| | | |
|---|---|---|
| EP | 2000551 | 12/2008 |
| EP | 2172234 | 4/2010 |
| WO | 2011051424 | 5/2011 |

OTHER PUBLICATIONS

EP12196260 European Search Report dated Dec. 23, 2014.

*Primary Examiner* — Seema Mathew
(74) *Attorney, Agent, or Firm* — Wagenkencht IP Law Group PC

(57) ABSTRACT

An implant, in particular an intraluminal endoprosthesis, or a semi-finished part for an implant, having a hollow cylindrical body, wherein the body includes magnesium, and the body is enriched with gallium or a gallium alloy in a region close to a surface.

10 Claims, 2 Drawing Sheets

Related U.S. Application Data

(60) Provisional application No. 61/601,564, filed on Feb. 22, 2012.

(51) Int. Cl.

| | | |
|---|---|---|
| *B21C 23/00* | (2006.01) | |
| *B21C 23/32* | (2006.01) | |
| *C22C 23/06* | (2006.01) | |
| *A61L 31/02* | (2006.01) | |
| *C10M 103/04* | (2006.01) | |
| *A61F 2/02* | (2006.01) | |
| *C10N 10/06* | (2006.01) | |
| *C10N 10/08* | (2006.01) | |
| *C10N 30/06* | (2006.01) | |
| *C10N 40/20* | (2006.01) | |

(56) References Cited

U.S. PATENT DOCUMENTS

| | | |
|---|---|---|
| 3,233,442 A | 2/1966 | Zvanut |
| 3,391,080 A | 7/1968 | Buckley et al. |
| 3,405,063 A | 10/1968 | Boes et al. |
| 3,427,244 A | 2/1969 | Boes |
| 6,613,088 B1 * | 9/2003 | Babizhayev .......... A61F 2/02 623/6.62 |
| 7,767,631 B2 | 8/2010 | Levy |
| 7,967,928 B2 | 6/2011 | Luo et al. |
| 8,453,665 B2 | 6/2013 | Braun et al. |
| 10,327,890 B2 * | 6/2019 | Bayer .......... A61L 27/50 |
| 10,518,001 B2 * | 12/2019 | Edick .......... C22C 23/02 |
| 10,772,746 B2 * | 9/2020 | Mangiardi .......... A61F 2/844 |
| 2003/0060695 A1 * | 3/2003 | Connelly .......... G01N 15/1456 600/365 |
| 2003/0129074 A1 * | 7/2003 | Bronfin .......... C22C 23/06 420/406 |
| 2004/0098108 A1 * | 5/2004 | Harder .......... A61F 2/91 623/1.15 |
| 2004/0241036 A1 * | 12/2004 | Meyer-Lindenberg .......... A61L 27/58 420/405 |
| 2005/0021127 A1 * | 1/2005 | Kawula .......... A61F 2/82 623/1.15 |
| 2005/0095166 A1 * | 5/2005 | Saikawa .......... C22C 23/02 420/407 |
| 2005/0266041 A1 * | 12/2005 | Gerold .......... A61L 31/022 424/423 |
| 2006/0052863 A1 * | 3/2006 | Harder .......... A61F 2/91 623/1.38 |
| 2006/0178697 A1 * | 8/2006 | Carr-Brendel ... A61B 17/12172 606/200 |
| 2007/0207186 A1 | 9/2007 | Scanlon et al. |
| 2008/0173057 A1 | 7/2008 | Kruger et al. |
| 2008/0184755 A1 | 8/2008 | Krajewski et al. |
| 2009/0032151 A1 | 2/2009 | Oishi et al. |
| 2009/0200177 A1 | 8/2009 | Furst et al. |
| 2010/0076544 A1 * | 3/2010 | Hoffmann .......... A61L 31/148 623/1.15 |
| 2011/0056429 A1 * | 3/2011 | Raring .......... C30B 29/406 117/101 |
| 2011/0126604 A1 | 6/2011 | Stork |
| 2011/0144761 A1 | 6/2011 | Rzany et al. |
| 2011/0180548 A1 | 7/2011 | Kuslitsky et al. |
| 2011/0226630 A1 * | 9/2011 | Wang .......... C25D 3/54 205/170 |
| 2012/0215301 A1 * | 8/2012 | Papirov .......... A61L 27/047 623/1.42 |
| 2013/0200391 A1 * | 8/2013 | Bedair .......... H01L 33/16 257/76 |
| 2013/0218292 A1 * | 8/2013 | Bayer .......... A61F 2/04 623/23.64 |
| 2013/0283882 A1 | 10/2013 | Sikora et al. |
| 2015/0084074 A1 * | 3/2015 | Bayram .......... H01L 33/32 257/94 |

\* cited by examiner

IMPLANT AND METHOD FOR PRODUCTION THEREOF

CROSS REFERENCE TO RELATED APPLICATIONS

This application is a divisional of U.S. Ser. No. 13/764,267, filed Feb. 11, 2013, which claims benefit of priority to U.S. provisional patent application Ser. No. 61/601,564 filed Feb. 22, 2012; the contents of which are herein incorporated by reference in their entirety.

TECHNICAL FIELD

The invention relates to a method for producing an implant, particularly an intraluminal endoprosthesis, and to an implant and a semifinished article for such an implant, each producible or produced by such a method.

BACKGROUND

Medical endoprostheses or implants for the widest range of applications are known in a wide variety from the prior art. Implants within the context of the present invention are understood as endovascular prostheses or other endoprostheses, for example, stents, bone attachment elements, for example, screws, plates or pins, surgical suture material, intestinal clamps, vascular clips, prostheses for hard and soft tissue, and anchor elements for electrodes, particularly for pacemakers or defibrillators.

Today, stents are used with particular frequency as implants for treating stenoses (vascular constrictions). They comprise a body in the form of a tubular or hollow cylindrical base lattice, which is open at both longitudinal ends. The tubular base lattice of an endoprosthesis of this type is inserted into the vessel to be treated, and serves to support the vessel. The use of stents to treat vascular diseases has become particularly common. By using stents, constricted areas of the vessels can be dilated, resulting in increased lumen. By using stents or other implants, an optimal vessel cross-section that is primarily necessary for treatment success can be achieved, however, the permanent presence of a foreign body of this type initiates a whole series of microbiological processes, which can lead to a gradual overgrowth of the stent and in the worst case to vascular obstruction.

One approach to solving this problem consists in producing the stent or other implants from a biodegradable material.

Biodegradation is understood to refer to hydrolytic, enzymatic and other metabolic degradation processes in a living organism, which are caused primarily by the bodily fluids coming into contact with the biodegradable material of the implant, and which lead to a gradual dissolution of the structures of the implant that contain the biodegradable material. This process causes the implant to lose its mechanical integrity at a certain time. The term biocorrosion is frequently used as a synonym for the term biodegradation. The term bioabsorption encompasses the subsequent absorption of the degradation products by the living organism.

Materials that are suitable for the body of biodegradable implants can contain polymers or metals, for example. The body can also consist of a plurality of such materials. The feature that is shared by these materials is their ability to biodegrade. Examples of suitable polymeric compounds are polymers from the group of cellulose, collagen, albumin, casein, polysaccharide (PSAC), polylactide (PLA), poly-L-lactide (PLLA), polyglycol (PGA), poly-D,L-lactide-co-glycolide (PDLLA-PGA), polyhydroxy butyric acid (PHB), polyhydroxy valeric acid (PHV), polyalkyl carbonates, polyortho esters, polyethylene terephthalate (PET), polymalic acid (PML), polyanhydrides, polyphosphazenes, polyamino acids and copolymers thereof, and hyaluronic acid. Each of the polymers can be used in pure form, in derived form, in the form of blends or as copolymers, depending upon the properties desired. The present invention relates to implants containing a metallic biodegradable material based upon magnesium or a magnesium alloy.

Stents that have coatings having different functions are already known in the art. Coatings of this type are used, for example, for releasing medications, positioning an x-ray marker, or protecting the structures that lie beneath said coatings.

In implementing biodegradable implants, the degradability thereof is controlled based upon the desired treatment or the use of the respective implant (coronary, intracranial, renal, etc.). For many therapeutic applications, for example, an important target range involves the implant losing its integrity over a period of four weeks to six months. In this context, integrity, i.e., mechanical integrity, is understood as the property that the implant has virtually no mechanical losses in relation to non-degraded implants. This means that the implant is still mechanically stable enough that, for example, the pressure to collapse drops only slightly, i.e., at most to 80% of the nominal value. Therefore, the implant is still able to perform, with maintenance of the integrity of its primary function, supporting the vessel. Alternatively, the integrity can be defined by the fact that the implant is mechanically stable enough that in its load state in the vessel, it is subject to almost no geometric changes, for example, it is not markedly compressed, i.e., under stress it retains at least 80% of its dilation diameter, or in the case of a stent, has almost no fractured supporting struts.

Biodegradable magnesium implants, particularly magnesium stents, have proven particularly promising for the stated target range of degradation, however, these implants still lose their mechanical integrity or supportive effect too early, and still have a severely fluctuating loss of integrity in vitro and in vivo. This means that with magnesium stents, the collapse pressure decreases too rapidly over time, or the decrease in the collapse pressure has too much variability and is therefore too indeterminable.

Various mechanisms for controlling the degradation of magnesium implants are already described in the prior art. These are based, for example, on inorganic and organic protective layers or combinations thereof, which offer resistance to the human corrosion milieu and the corrosive processes occurring therein. Solutions known in the prior art are characterized in that boundary layer effects are achieved, which involve a spatial and, if possible, defect-free separation of the corrosive medium from the metallic material, particularly the metallic magnesium. For instance, protection against degradation is ensured by various combined protective layers and by defined geometric distances (diffusion barriers) between the corrosive medium and the magnesium base material. Additional solutions in the field of controlled degradation produce predefined fracture effects by the application of physical (e.g., localized cross-sectional changes) and/or chemical changes to the stent surface (e.g., localized chemically differently composed multilayers). However, the above-mentioned solutions have as yet failed, for the most part, to place the dissolution produced by the degradation process and the resulting strut breaks within the required window of time. The result is degradation of the implant that begins either too early or too late, or is too widely variable.

A further problem associated with coatings results from the fact that stents or other implants ordinarily take on two states, specifically a compressed state in which they have a small diameter, and a dilated state, in which they have a larger diameter. In the compressed state, the implant can be inserted by means of a catheter into the vessel to be supported, and can be positioned at the site to be treated. At the treatment location, the implant is then dilated by means of a balloon catheter, for example. This change in diameter subjects the body of the implant to mechanical stress. Additional mechanical stresses on the implant can occur during production or with the movement of the implant in or with the vessel into which the implant is inserted. Therefore, with the stated coatings according to the prior art, the disadvantage results that the coating tears (e.g., formation of microcracks) or is even partially removed during deformation of the implant. This can result in an unspecified localized degradation. In addition, the onset and the speed of degradation are dependent upon the size and the distribution of the microcracks resulting from the deformation, which as defects cannot be easily controlled. This results in a large deviation in degradation times.

Additional examples of known organic or inorganic protective layers for increasing resistance to degradation include galvanic coatings with zinc, coatings based on ionic liquids, conversion coatings involving chemical conversion of the main alloy constituents, vaporization or sputtering with aluminum, thermal spraying, etc.

Higher alloyed parent materials are also used for improving resistance to degradation. For instance, for years, magnesium alloys containing rare earths (e.g., alloy WE 43) have been used as stent material. For many applications, these materials have an advantageous combination of adequate mechanical properties and good corrosion resistance. Therefore, they have a greater potential for use in absorbable implants as compared with non-alloyed magnesium.

From document WO 2011/051424 A1, an implantable medical device is known, which is made at least partially of a material that contains highly pure magnesium or a magnesium alloy with highly pure magnesium and one or more additional highly pure alloy constituents. Highly pure alloy constituents can be the elements indium, scandium, yttrium, gallium and the rare earths, wherein highly pure gallium is present in the alloy in amounts of 0.1 wt % to 5 wt %. The production of such highly pure materials is very costly, and therefore, the costs of the medical apparatus are also high.

Document WO 2007/0207186 A1 lists a series of additives which improve the properties of an implant. In this case, however, the modified properties of the implant are not described in detail in terms of the respective additive.

SUMMARY

The problem addressed by the present invention is therefore that of indicating a cost-effective method for producing an implant, in which the degradation of the implant proceeds more slowly.

The degradation is also to take place within a time period that can be better controlled. The invention therefore also addresses the problem of devising an implant of this type.

The problem stated above is solved by a method in which the implant is produced from a preferably hollow cylindrical semifinished article, wherein the semifinished article contains magnesium or a magnesium alloy, the method including the following steps:

a) preparing the semifinished article and
b) shaping the semifinished article at a temperature of between 250° C. and 550° C. by means of a tool, which has a metallic lubricant containing gallium and/or a gallium compound (including gallium alloy) on at least a part of its surface that will come into contact with the semifinished article.

In the present invention, shaping is carried out at a temperature above 250° C., preferably above 300° C., particularly preferably above 350° C. The upper limit for the shaping temperature is approximately 550° C., since above 550° C. structural parts of the implant become molten and losses with respect to the mechanical stability of the end product (implant) may occur.

The necessary minimization of friction between the material to be shaped and the tool, preferably for the extrusion shaping process, is achieved by means of the lubricant used according to the method of the invention. The lubricant is fluid above room temperature and, as a result of its viscosity, has a low shear stability, so that an effective lubricating effect is achieved. It is further advantageous that within the temperature range, the lubricant has only a low vapor pressure and only an insignificant change in viscosity.

In addition to the lubricating function, the lubricant also has the special property that during shaping, particularly during an extrusion process, it diffuses into the surface of the semifinished article and becomes alloyed with it. The high diffusion speed which occurs at the increased temperatures that are used leads to alloy formation on the surfaces of the semifinished article already during the process time. The depth and the stoichiometric composition of the alloyed surface region (region close to the surface, surface zone) are determined by the process parameters of the shaping process (e.g., the shaping speed, the temperature, the quantity of lubricant, the composition of the lubricant (e.g., in the case of extrusion)), and a subsequent tempering treatment, which can vary in terms of temperature and duration. The element gallium, which is dominant in the lubricant, results, by way of alloy formation with magnesium, in a modified implant with respect to its mechanical and biochemical properties, which will be described below in detail.

Therefore, the lubricant has multifunctional properties.

The lubricant used in the method according to the invention is used in place of the conventional lubricant graphite or molybdenum disulfide, which cannot be removed without residue from the semifinished article surface or the regions close to the surface. Moreover, under the traditional process parameters, particularly during extrusion, these conventional lubricants react in an undesirable manner with the surface of the magnesium-containing base material, and form firmly adhering crusts, which consist of compounds of the elements contained in these lubricants, for example, C, O, Mo, S, with magnesium. These crusts must be eliminated at high cost during the subsequent process in production of the implant, for example, by means of reaming, corundum blasting, scouring and/or electropolishing. However, because these crusts do not form during the method according to the invention, the stated elimination steps also are unnecessary, and therefore, the production of the implant is cost-effective and simple.

An implant can then be produced in a simple manner from the stated semifinished article, said implant having an absorbable gradient material, and being characterized by a series of advantages in terms of its degradation behavior over implants made of conventional material.

The implant has improved mechanical properties, e.g., better behavior during shaping, and an improved dynamic load-bearing capacity due to a reduced susceptibility to cracking induced by surface defects under dynamic stress. More particularly, an implant of this type is less susceptible to fracturing under dilation (e.g., with dilation of a stent). For instance, it has been found that the average diameter of the first strut fracture with dilation of a stent of a specific design could be increased from 4.6 mm (reference untreated) to 4.9 mm (solution according to the invention).

Moreover, by using the gallium to adjust the electrochemical surface potential, the degradation speed is adjusted toward longer degradation times, wherein the desired lower degradation speed can be adjusted by modifying the diffusion depth and/or the alloy composition.

In addition, the degradation speed can be controlled by varying the layer thickness. This also opens up the possibility of adjusting the degradation duration of the implant at the specific implantation site (coronary, intracranial, renal, etc.). It has further been observed that the period of degradation is advantageously extended from a previous 4 to 6 months (uncoated reference) to a current 7 to 8 months (solution according to the invention). Furthermore, cost savings can be realized in the manufacturing process of the implant, because the semifinished article can be better further processed, since slag adhesions, which occur, for example, at the cutting edge during laser cutting of the implant, can be removed more easily.

In addition, the semifinished article produced by way of the method according to the invention has an improved surface quality over that of known semifinished articles, resulting in a more uniform removal of the surface layer in a subsequent electropolishing step. If applicable, the improved surface quality also permits a permanent adhesion to or a uniform coating of the surface with polymers.

In contrast, semifinished articles produced by conventional means, for example, by plating methods, frequently exhibit delaminations of an applied layer from the base body during deformation of the end products produced therefrom, for example, during dilation of a stent.

During the shaping step, the lubricant, which is disposed between tool wall and semifinished article, diffuses into the magnesium surface of the semifinished article. As the temperature/time diagram of the magnesium/gallium system illustrated in FIG. 2 demonstrates, the magnesium/gallium system possesses a eutectic mixture at 423° C. and 19 atom % gallium, and a maximum solubility of approximately 8 wt % gallium in magnesium exists at 423° C. A solubility of this type shows that an alloy of magnesium and gallium can be formed. After the shaping process, the non-alloyed, excess gallium and/or lubricant can be stripped both from the tool and from the semifinished article.

A further advantage of the implant produced by the method according to the invention consists in that said implant has improved biocompatibility, since the chemical surface composition can be adjusted in relation to the respective tissue or bodily fluid on both the luminal and abluminal sides of the implant.

In a preferred embodiment example, the shaping comprises an extrusion step, which is carried out within a suitable temperature range for the solubility of the gallium in magnesium.

A particularly suitable lubricant for use in the method according to the invention is GALINSTAN, which is a silvery, eutectic alloy of gallium, indium and tin. GALINTSAN is fluid at room temperature and, according to the information from the manufacturer, Geratherm Medical AG, Geschwenda, Germany, it transitions to the solid state of aggregation at temperatures below 19° C. GALINTSAN consists of 65 to 95% gallium, 5 to 22% indium and 0 to 11 wt % tin.

For alloying the gallium, it is advantageous for shaping to be carried out at least intermittently, preferably over at least 30 seconds, at a temperature of at least 300° C. At process temperatures of at least 300° C., mixed phases of magnesium and gallium are produced, which form according to the binary phase diagram, dependent upon the process residence time of several minutes, to depths of 40 μm. The structure consisting in this case of magnesium/gallium mixed crystals is distinguished from a purely metallic magnesium matrix by an increased resistance to corrosion and an increased resistance to fracturing.

Furthermore, because of the property that, on the basis of diffusion processes, the concentration of the gallium of the semifinished article surface in the depth of the material decreases, an "interleaving" of the gallium-rich region close to the surface of the semifinished article and of the base material (without gallium) of the semifinished article is achieved, so that, in the implant produced from this, advantageously no delaminations of the gallium-rich layer close to the surface occur under bending, shearing, and torsion stresses in the conditions of use of the implant.

In a further improvement of the invention, following the shaping process, a tempering step is carried out at at least 300° C. over a period of at least 1 minute, and the semifinished article is then preferably air cooled, preferably at room temperature. This tempering step serves to break down internal mechanical stresses contained in the structure following shaping. If this low-stress annealing process were not carried out, undesirable geometric deformations of the semifinished article would occur, which would have a negative effect on subsequent processing steps (e.g., wobbling in the laser clamping device and the associated increased imprecision during laser cutting).

Further processing steps toward finishing the implant include deburring, scouring and/or electropolishing. These steps can lead to a reduction in the layer thickness of the boundary layer enriched with gallium.

The above problem is also solved by a semifinished article for the production of an implant, wherein the semifinished article comprises magnesium or a magnesium alloy, obtainable or obtained by one of the above-described methods.

Accordingly, the above problem is also solved by an implant having an implant body, wherein the implant body contains magnesium or a magnesium alloy, obtainable or obtained by one of the methods described in the above claims.

The above problem is also solved by an implant, particularly an intraluminal endoprosthesis, having a body, wherein the body contains magnesium or a magnesium alloy and gallium and/or a gallium alloy in a region close to the surface.

For the implant according to the invention, it is advantageous that, according to the above method according to the invention, the lubricant containing gallium or a gallium compound achieves the necessary minimization of friction between the material to be shaped and the tool. On the other hand, in a region of the semifinished article or the implant that is close to the surface thereof is a layer in which gallium (from the lubricant) forms an alloy constituent for the magnesium already present in the semifinished article or implant body. The excess gallium not involved in alloy formation can be easily removed from the surface of the semifinished article. In addition to the advantages already described above, an implant produced from the semifinished article also has increased tolerance to damage in the presence of interior nicks, for example, caused by enclosures and stringers of intermetallic compounds of the magnesium with typical alloy elements.

This effect is based upon the greater plastic deformability of gallium-rich particles of the implant structure, which are capable, under mechanical stress, of activating additional slide planes. In other words, if cracks originating from interior nicks extend into the particles of the implant structure that are alloyed with gallium, a plastic deformation of the particles and a formation of slide bands will first result. In contrast, in an implant whose semifinished article is not shaped during the manufacturing process using a gallium-containing lubricant, incipient cracks will change to a microscopic crack, resulting in earlier strut fracture.

The region close to the surface with the gallium or the gallium compound in the resulting implant preferably has a thickness of at least 10 µm, particularly preferably of at least 15 µm, more preferably a maximum of 40 µm.

The body of the implant comprises at least a part of the implant, preferably the main part of the implant, which provides the mechanical integrity of the implant. The present invention therefore relates particularly to implants, the material of the body of which contains magnesium as the main constituent and is preferably biodegradable.

In a further preferred embodiment example, the implant body is treated electrochemically following the laser cutting and deburring, and is preferably electrochemically polished. In this manner, contaminants on the surface of the implant body are removed. Electropolishing results in low-contamination cover layers based upon greater material removal effects (depth effect).

In what follows, the method according to the invention will be specified in greater detail in reference to examples and figures. In this, all illustrated and/or described features form the subject matter of the invention, irrespective of the summary thereof in the claims or in the dependency references thereof.

DETAILED DESCRIPTION

Figure 1:
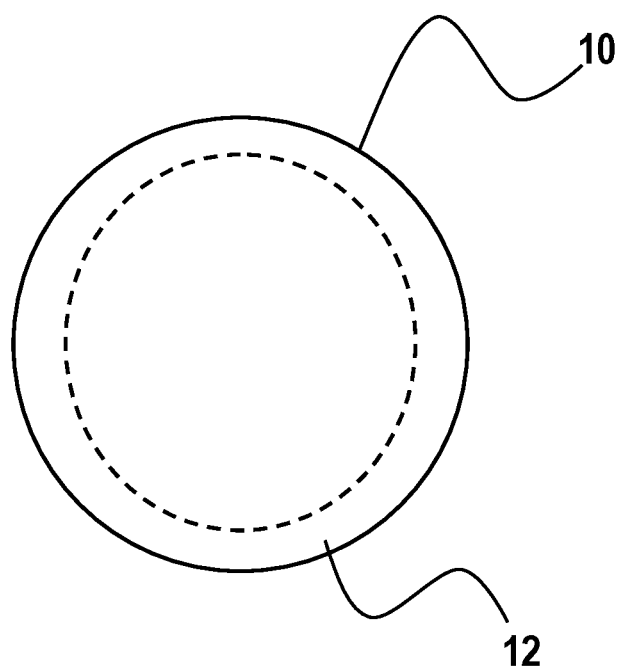
FIG. 1 a cross-section of a semifinished article according to the invention (for example, for a stent) according to step b) of the method according to the invention, and FIG. 2 the binary status diagram for the magnesium/gallium system.

It should first be noted that the indications of concentrations of a material contained in the following description are given in wt %, unless otherwise indicated at the relevant site.

A tubular or hollow cylindrical sleeve made of a magnesium alloy, for example, having the composition WE 43 (4% Y, 2% Nd, 0.5% Gd, 0.5% Dy, 0.5% Zr, remainder Mg) is subjected to an extrusion process for the purpose of producing an implant semifinished article, for example, for a stent. Prior to the extrusion process, GALINTSAN having a composition of 68.5% Ga, 21.5% In and 10% Sn, by way of example, is applied to the surface of the extrusion tool as a lubricant, in places where the surface of the extrusion tool will come into contact with the sleeve. In addition, the ram that will determine the interior geometry and/or the die that will determine the later outer surface can also be provided with the lubricant.

The gallium-containing lubricant is applied in the form of drops to the outer tool (ram) and/or to the inner tool (die) prior to the extrusion process. The tools and the blank, which is arranged on the ram and will be shaped (dimensions, e.g., outer diameter 3 mm to 10 mm, inner diameter 1 mm to 5 mm, length 3 mm to 15 mm), are then heated to the process temperature, which lies between 300° C. and 500° C. The heating process lasts approximately 1 minute to 10 minutes. This is followed by the actual shaping process, in which the cylindrical blank arranged on the ram is extruded in the die to a semifinished article 10 in the form of a sleeve (dimensions, e.g., outer diameter 2 mm, inner diameter 1.6 mm, length 50 mm to 200 mm). The press speed can range between 1 mm/min and 100 mm/min, for example, so that the extrusion process is completed after approximately 30 seconds to 200 minutes.

With the introduction of the ram into the blank (also called the slug) situated in the die and the preceding heating of the sleeve to the process temperature of approximately 400° C., gallium first imparts its effect as a lubricant due to its extremely low shear forces, which are particularly pronounced in the molten state.

During shaping, the elements of the gallium-containing lubricant diffuse into the resulting new inner and/or outer surface of the semifinished article 10, and begin to form an alloy with the magnesium.

The extruded semifinished article 10 is then removed from the tool and cools within a few minutes to nearly room temperature.

This is followed by a tempering step, preferably at 300° C. to 500° C., for eliminating stresses (so-called low-stress annealing), over a period of 1 minute to 60 minutes in air or under inert gas such as argon. In this, two processes take place in the zones close to the surface. For one, the diffusion of the elements of the lubricant into the volume of the semifinished article continues, and for another, an alloy of Mg and Ga forms. In this process, either the gallium becomes partially embedded in the Mg lattice as a substituent in accordance with the binary status diagram Mg/Ga illustrated in FIG. 2, or intermetallic compounds, e.g., $Mg_5Ga_2$, $Mg_2Ga$ and $MgGa$ form in a region 12 (or layer) close to the surface. As a result, mixed phases are produced, which form according to the phase diagram (see FIG. 2) on the basis of the process holding time of several minutes, to a depth of up to 40 µm. By adjusting the above-described process parameters of temperature and time, the diffusion depth of the gallium into the semifinished article can be varied to an order of magnitude of between 20 µm (at 450° C./10 min) and 40 µm (470° C./40 min), measured from the respective surface of the semifinished article.

FIG. 1 shows the increased gallium concentration in the boundary region 12 close to the surface, on only the abluminal side. Depending upon the application of the lubricant in the tool, the luminal side of the semifinished article can alternatively or additionally have a boundary region of this type close to the surface with an increased gallium concentration.

An overdosing of lubricant is not possible, because at the end of the process, excess lubricant either remains on the tool or is stripped off of it.

The additional process steps are structured similarly to the known methods for producing implants by means of laser beam methods, which have been described many times, and comprise final shaping processes such as laser cutting, deburring, scouring and electropolishing. It is particularly important to mention within this context that the scouring and electropolishing steps are run in phosphoric acid-containing solutions at room temperature, over periods of between 0.5 minutes and 4 minutes (preferably 2 minutes). The scouring and electropolishing include a removal of material. For example, the removal of material by scouring over a period of 2 minutes amounts to between 10 µm and 20 µm of the wall thickness. Therefore, at the end of the production process the implant, e.g., the stent, still has a wall thickness of between 140 µm and 170 µm, wherein the wall thickness of the semifinished article, after extrusion and tempering and before electropolishing and/or scouring, amounts to 180 µm to 190 µm. However, when the described process parameters are applied, it is ensured that the diffusion depth of the gallium in the magnesium matrix material is greater than the removal of material that occurs as a result of the scouring and/or polishing step.

The finished implant, similarly to the semifinished article 10, also has an increased gallium concentration in a boundary region, close to the surface, of the outer side and/or the inner side of its struts.

It is advantageous that this is achieved in the semifinished article 10 as a result of the "interleaving", produced in a metallurgical process, in the region close to the surface that is rich with gallium, with the base material. This means that in the finished implant, no delamination phenomena occur with bending, shearing or torsion stress under the conditions of use of the implant.

Figure 2:
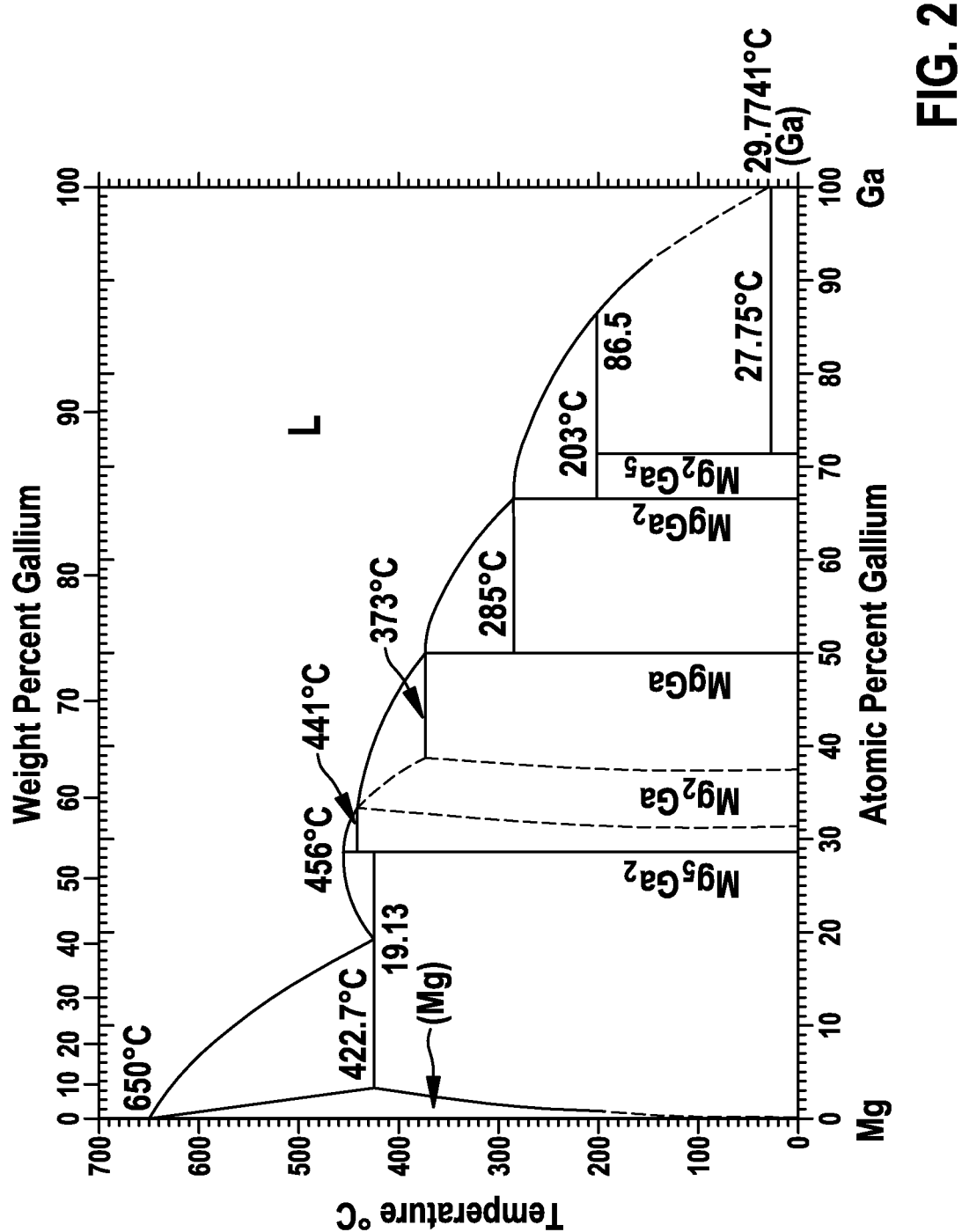

As was already mentioned above, the binary status diagram for the gallium/magnesium system is illustrated in FIG. 2, wherein the gallium concentration in wt % or atom % is plotted on the X axis and the temperature in ° C. is plotted on the Y axis. The letter L is used to identify the liquid range.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

10 Semifinished article
12 Region close to the surface
L Liquid range

What is claimed is:

1. An intraluminal endoprosthesis comprising a body that comprises a WE 43 magnesium alloy characterized as 4%, Y, 2%, Nd, 0.5% Gd, 0.5% Dy, 0.5% Zr, and a remainder Mg, and the body is enriched with a gallium alloy in a region close to a surface.

2. The intraluminal endoprosthesis according to claim 1, wherein the endoprosthesis has a hollow cylindrical body.

3. An intraluminal endoprosthesis comprising a body that comprises magnesium, and the body is enriched with a gallium alloy in a region close to a surface.

4. The endoprosthesis according to claim 3, the body further comprising a polymer coating.

5. The intraluminal endoprosthesis according to claim 3, wherein the endoprosthesis has a hollow cylindrical body.

6. An implant, in particular an intraluminal endoprosthesis, comprising a body that comprises magnesium, and the body is enriched with a gallium alloy in a region close to a surface, wherein the gallium alloy comprises indium, tin and 65 to 95% gallium.

7. An implant, in particular an intraluminal endoprosthesis that comprises magnesium, and the body is enriched with gallium or a gallium alloy in a region close to a surface, wherein the region close to the surface comprises a depth of up to 40 µm from the surface.

8. The implant according to claim 7, wherein the region close to the surface comprises a depth of at least 10 µm from the surface.

9. The implant according to claim 7, wherein the depth is at least 15 µm from the surface.

10. An intraluminal endoprosthesis comprising a body that comprises magnesium, and the body is enriched with a gallium alloy in a region close to a surface, the gallium alloy comprising 65 to 95% gallium.

* * * * *